United States Patent
Song et al.

(10) Patent No.: US 9,029,077 B2
(45) Date of Patent: May 12, 2015

(54) MANUFACTURING METHOD FOR FIBROUS DEMINERALIZED BONE MATRIX

(75) Inventors: Seok-Beom Song, Gyeonggi-do (KR);
Goo-Won Jeong, Seoul (KR);
Jung-Won So, Gyeonggi-do (KR);
Han-Sol Seo, Jeollabuk-do (KR);
Hyun-Seung Ryu, Gyeonggi-do (KR);
Giue-Nam Kim, Seoul (KR);
Byoung-Suck Kim, Seoul (KR)

(73) Assignee: CG Bio Co., Ltd., Kyunggi-Do (KR)

( * ) Notice: Subject to any disclaimer, the term of this patent is extended or adjusted under 35 U.S.C. 154(b) by 0 days.

(21) Appl. No.: 14/347,601

(22) PCT Filed: Oct. 11, 2011

(86) PCT No.: PCT/KR2011/007517
§ 371 (c)(1),
(2), (4) Date: Mar. 26, 2014

(87) PCT Pub. No.: WO2013/047936
PCT Pub. Date: Apr. 4, 2013

(65) Prior Publication Data
US 2014/0208980 A1    Jul. 31, 2014

(30) Foreign Application Priority Data
Sep. 29, 2011    (KR) .................. 10-2011-0099016

(51) Int. Cl.
| A61L 27/36 | (2006.01) |
| A61F 2/28 | (2006.01) |
| A61F 2/46 | (2006.01) |

(52) U.S. Cl.
CPC ......... *A61L 27/3683* (2013.01); *A61L 27/3608* (2013.01); *A61L 2430/02* (2013.01); *A61F 2002/2839* (2013.01); *A61F 2002/4645* (2013.01)

(58) Field of Classification Search
IPC ....................... A61L 27/3608,27/3687, 27/3691
See application file for complete search history.

(56) References Cited

U.S. PATENT DOCUMENTS

| 5,607,269 A | 3/1997 | Dowd |
| 7,323,193 B2 | 1/2008 | Morris |
| 7,939,108 B2 | 5/2011 | Morris |
| 2004/0023387 A1 | 2/2004 | Morris |
| 2008/0154386 A1 | 6/2008 | Morris |
| 2011/0108644 A1 | 5/2011 | Morris |
| 2012/0093895 A1 | 4/2012 | Song et al. |

FOREIGN PATENT DOCUMENTS

| KR | 1020080106286 A | 5/2010 |
| KR | 1020110000485 B1 | 1/2011 |

*Primary Examiner* — Rosanne Kosson
(74) *Attorney, Agent, or Firm* — Vorys, Sater, Seymour and Pease LLP; Mihsun Koh

(57) ABSTRACT

The present invention relates to a manufacturing method for fibrous demineralized bone matrix, the method comprising: (a) a step for subjecting a bone, separated from a body, to a primary demineralization in an acid solution for 1-5 hours; (b) a step for slicing the bone obtained in step (a) to a thickness of 0.1-3 mm, thus forming a sheet of bone; (c) a step for subjecting the sheet of bone obtained in step (b) to a secondary demineralization in an acid solution for 2-6 hours; and (d) a step for grinding the demineralized bone obtained in step (c).

4 Claims, 2 Drawing Sheets

MANUFACTURING METHOD FOR FIBROUS DEMINERALIZED BONE MATRIX

TECHNICAL FIELD AND SUMMARY OF THE INVENTION

The present invention relates to an improved process for preparing a fibrous demineralized bone matrix, more specifically to an improved process for preparing a fibrous demineralized bone matrix, comprising steps for partial demineralizing, slicing, complete demineralizing, and pulverizing.

BACKGROUND ART

Demineralized bone matrix (DBM) refers to a bone whose minerals have been removed by adding it to an acid. Demineralized bone matrix mostly consists of highly cross-linked collagen and comprises the remaining non-collagenic proteins such as TGF-β, PDGF, osteopontin, osteonectin, bone morphogenetic protein (BMP) and the like. Demineralized bone matrix is used in a composition for bone implants, in the repair of bone defects, etc.

Demineralized bone matrix is obtained in a particulate form, through demineralizing a bone externally discharged from a body, followed by pulverizing into an appropriate size. The present inventors have disclosed a bone-repair composition comprising a demineralized bone matrix having a particle size of 0.05 to 250 μm; a demineralized bone matrix having a particle size of 250 to 2000 μm; and a hydrating material, wherein the demineralized bone matrixes are mixed in a certain ratio. The bone-repair composition has excellent injectability and shape-maintenance (handling) properties (Korean Patent No. 10-1041784).

Meanwhile, cortical bone consists of collagen fiber bundles that are oriented parallel to the long axis thereof. It is known that the fibrous demineralized bone matrix obtained therefrom exhibits properties useful for implants intended for use in bone repairs and other orthopedic applications. The fibrous demineralized bone matrix is prepared by milling a cortical bone externally discharged from a body with a special milling machinery until a particle having a fiber form is obtained, followed by demineralizing the resulting particles (U.S. Pat. No. 5,607,269). However, there are some drawbacks, e.g., that such a method needs to use only intact cortical shafts as a bone source, because of the mechanical limitations of the bone milling machinery; and that the yield of the fibrous demineralized bone is very low. In order to address said problems, U.S. Pat. Nos. 7,323,193 and 7,939,108 have disclosed a process for preparing a fibrous demineralized bone matrix, comprising demineralizing the bone sections obtained from a bone externally discharged from a body in an acidic solution for 6 hours, demineralizing the resultant in an acidic solution for two days, and then pulverizing the demineralized bone sections. However, the processes disclosed in U.S. Pat. Nos. 7,323,193 and 7,939,108 have a drawback that the demineralizing step needs to be performed for long time, i.e., for two days (48 hours).

DETAILED DESCRIPTION OF THE INVENTION

Technical Problem

The present inventors have performed various researches for developing processes for preparing a fibrous demineralized bone matrix having useful properties, especially for developing processes in order to improve the demineralizing step requiring a long time. As a result, when partially demineralized bone is sliced to form a bone in a thin sheet form, which is then demineralized, it is surprisingly found that the demineralizing step can be remarkably reduced to about 6 hours; and that the resulting fibrous demineralized bone matrix can be obtained in high yield.

Therefore, it is an object of the present invention to provide a process for preparing a fibrous demineralized bone matrix, comprising sequential steps for partial demineralizing, slicing, complete demineralizing, and pulverizing.

Technical Solution

According to an aspect of the present invention, there is provided a process for preparing a fibrous demineralized bone matrix, the process of which comprises: (a) performing a first demineralizing step by demineralizing a bone externally discharged from a body in an acidic solution for 1 to 5 hours; (b) slicing the bone obtained from the step (a) to form a bone in a sheet form having a thickness of 0.1 to 3 mm; (c) performing a second demineralizing step by demineralizing the bone in a sheet form obtained from the step (b) in an acidic solution for 2 to 6 hours; and (d) pulverizing the demineralized bone obtained from the step (c).

In the process for preparing a fibrous demineralized bone matrix, the acidic solutions in the steps (a) and (c) may be, independently each other, a 0.1 to 3 N HCl solution, preferably a 0.6 N HCl solution. And also, the pulverizing may be carried out so as to obtain a demineralized bone matrix having a length ranging from 1000 to 5000 μm.

Advantageous Effects

It is newly found by the present invention that, through performing sequential steps for partial demineralizing, slicing, complete demineralizing, and pulverizing, the demineralizing step can be remarkably reduced to about 6 hours. Especially, it is found by the present invention that, through incorporating a slicing step, the resulting demineralized bone matrix can be obtained in high yield as a demineralized bone matrix having a fiber form, in addition to reduction of the time for demineralization. Therefore, the process according to the present invention may be suitably applied to industrial mass production.

BEST MODE FOR CARRYING OUT THE INVENTION

Figure 1:
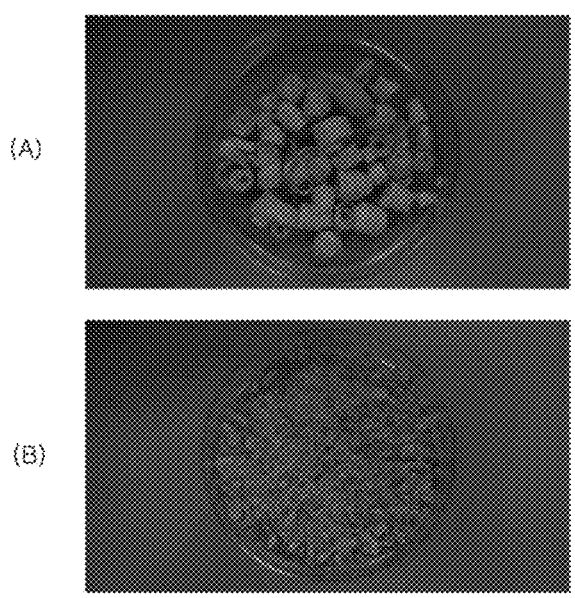
FIG. 1 shows the bones obtained by slicing a partially demineralized bone (A) and the bones obtained by pulverizing a demineralized bone (B).

The present invention provides a process for preparing a fibrous demineralized bone matrix, the process of which comprises: (a) performing a first demineralizing step by demineralizing a bone externally discharged from a body in an acidic solution for 1 to 5 hours; (b) slicing the bone obtained from the step (a) to form a bone in a sheet form having a thickness of 0.1 to 3 mm; (c) performing a second demineralizing step by demineralizing the bone in a sheet form obtained from the step (b) in an acidic solution for 2 to 6 hours; and (d) pulverizing the demineralized bone obtained from the step (c).

The process of the present invention includes performing sequential steps for partial demineralizing, slicing, complete demineralizing, and pulverizing. Especially, through introducing the steps for partial demineralizing and slicing, the time for the subsequent demineralizing step can be remarkably reduced to about 6 hours; and the resulting demineralized bone matrix can be obtained in high yield as a demineralized bone matrix having a fiber form.

The process of the present invention includes a partial demineralizing step, i.e., performing a first demineralizing step by demineralizing a bone externally discharged from a body in an acidic solution for 1 to 5 hours [that is, the step (a)]. The bone externally discharged from a body may be a bone derived from a mammal, including a human. It is preferable to use the bone obtained after removing soft tissues, lipids, bone marrow, etc. from the bone externally discharged from a body, according to conventional methods. The removing may be carried out using e.g., 60 to 90 wt/wt % ethanol solution. If necessary, a surfactant may be additionally used. Typically, the acidic solution may be a HCl solution such as a 0.1 to 3 N HCl solution, preferably about a 0.6 N HCl solution. And also, the first demineralizing step may be performed for 1 to 5 hours, preferably about 3 hours.

The process of the present invention includes a step for slicing the partially demineralized bone into a sheet form, i.e., slicing the bone obtained from the partial demineralizing step to form a bone in a sheet form having a thickness of 0.1 to 3 mm [that is, the step (b)]. The slicing may be performed with an appropriate apparatus for thinly cutting a bone, for example with a bone slicer such as Bone Slicer (YOU IL MC/CO. KR), but not limited thereto. The thickness of the bone in a sheet form obtained by said slicing may range from 0.1 to 3 mm, preferably from 0.2 to 1.0 mm, more preferably from 0.3 to 0.6 mm, most preferably about 0.5 mm. When the thickness exceeds 3.0 mm, broken particulate forms (not a sheet form) may be obtained. When the thickness is below 0.1 mm, a sheet form can be obtained; but subsequent demineralization of the resulting sheet form may give particulate forms (not a fiber form).

The process of the present invention includes a step for completely demineralizing the partially demineralized bone in a sheet form, i.e., performing a second demineralizing step by demineralizing the bone in a sheet form obtained from the above step in an acidic solution for 2 to 6 hours [that is, the step (c)]. Typically, the acidic solution may be a HCl solution such as a 0.1 to 3 N HCl solution, preferably about a 0.6 N HCl solution. It is found by the present invention that the second demineralizing step, i.e., complete demineralizing step, can be performed in a remarkably reduced time (i.e., in 2 to 6 hours, preferable in about 3 hours), in comparison with known demineralizing methods.

The process of the present invention includes a step for pulverizing the completely demineralized bone [that is, the step (d)]. The pulverizing may be performed with a conventional pulverizing apparatus. The pulverizing may be carried out so as to obtain a fibrous demineralized bone matrix having a length ranging from 1000 to 5000 μm, preferably from 2,000 to 4,000 μm, which can be accomplished by setting appropriate pulverizing conditions according to types of the pulverizing apparatus used.

The present invention will be described in further detail with reference to the following examples. However, these examples are for illustrative purposes only and are not intended to limit the scope of the present invention.

Example 1

Figure 2:
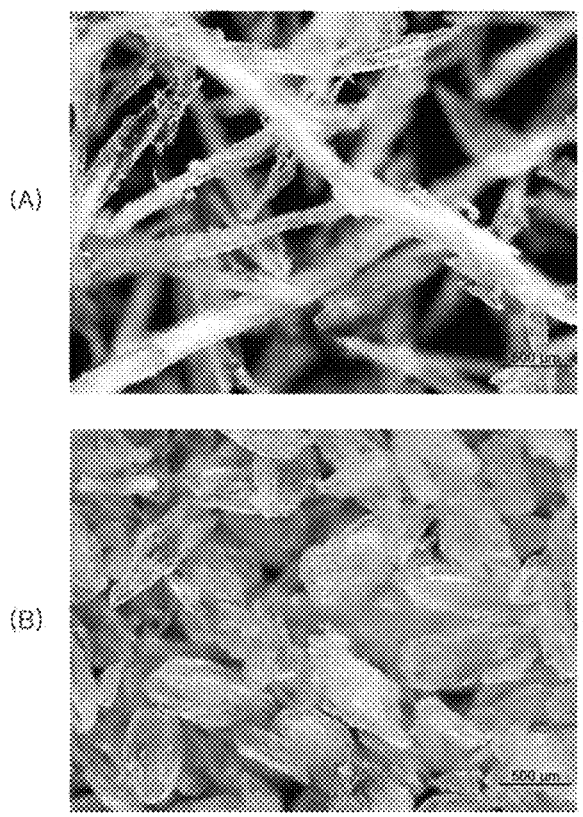
FIG. 2 shows the pictures obtained by observing with an optical microscope the demineralized bone matrix in a fiber form (A) and the demineralized bone matrix in a particulate form (B).

From a bone (weight: about 172 g) of human donor origin, soft tissues attached to the bone were removed with a surgical instrument; and then impurities such as soft tissues, lipids, and bone marrow were removed using a tissue detergent containing a surfactant. The resulting bone was cut into a half. The cut bones were placed in 20 ml of a 0.6N HCl solution per 1 g of the bone for 3 hours, for partial demineralization. The partially demineralized bones were isolated and then placed in 20 ml of distilled water per 1 g of the bone, so as to remove the demineralizing solution in the bones. The resulting bones were sliced with a bone slicer (YOU IL MC/CO. KR) into a sheet form having a thickness of about 0.5 mm. The resulting bones in a sheet form are shown in FIG. 1 (A). The resulting bones in a sheet form were placed in 30 ml of a 0.6N HCl solution per 1 g of the bone for 3 hours, for complete demineralization. The precipitated demineralized bone matrix was isolated, pulverized with a pulverizing apparatus (IKA, M20 Universal mill, GR) for about 10 minutes, neutralized with phosphate buffered saline (PBS), washed with distilled water, and then lyophilized to obtain about 31 g of the demineralized bone matrix. The picture obtained by observing the resulting demineralized bone matrix with an optical microscope is shown in FIG. 2 (A). From the result of FIG. 2 (A), it can be seen that the resulting demineralized bone matrix is a demineralized bone matrix having a fiber form.

Comparative Example 1

From a bone (weight: about 165 g) of human donor origin, soft tissues attached to the bone were removed with a surgical instrument; and then impurities such as soft tissues, lipids, and bone marrow were removed using a tissue detergent containing a surfactant. The resulting bone was cut into a half. The cut bones were placed in 20 ml of a 0.6N HCl solution per 1 g of the bone for 3 hours, for partial demineralization. The partially demineralized bones were isolated and then placed in 20 ml of distilled water per 1 g of the bone, so as to remove the demineralizing solution in the bones. The resulting bones were again placed in 30 ml of a 0.6N HCl solution per 1 g of the bone for 3 hours, for demineralization. However, because the demineralization was hardly processed, we could not obtain a demineralized bone matrix.

Comparative Example 2

From a bone (weight: about 192 g) of human donor origin, soft tissues attached to the bone were removed with a surgical instrument; and then impurities such as soft tissues, lipids, and bone marrow were removed using a tissue detergent containing a surfactant. The resulting bone was cut into a half. The cut bones were placed in 20 ml of a 0.6N HCl solution per 1 g of the bone for 3 hours, for partial demineralization. The partially demineralized bones were isolated and then placed in 20 ml of distilled water per 1 g of the bone, so as to remove the demineralizing solution in the bones. The resulting bones were pulverized with a pulverizing apparatus (IKA, M20 Universal mill, GR) for about 60 minutes to obtain pulverized bones, which are shown in FIG. 1 (B). The pulverized bones were placed in 30 ml of a 0.6N HCl solution per 1 g of the bone for 3 hours, for complete demineralization. The precipitated demineralized bone matrix was isolated, neutralized with phosphate buffered saline (PBS), washed with distilled water, and then lyophilized to obtain about 36.4 g of the demineralized bone matrix. The picture obtained by observing the resulting demineralized bone matrix with an optical microscope is shown in FIG. 2 (B). From the result of FIG. 2 (B), it can be seen that the resulting demineralized bone matrix is a demineralized bone matrix having a particulate form.

The invention claimed is:

1. A process for preparing a fibrous demineralized bone matrix, comprising:
   (a) performing a first demineralizing step by demineralizing a bone removed from a body in an acidic solution for 1 to 5 hours;
   (b) slicing the bone obtained from step (a) to form a bone in a sheet form having a thickness of 0.1 to 3 mm;
   (c) performing a second demineralizing step by demineralizing the bone in the sheet form obtained from step (b) in an acidic solution for 2 to 6 hours; and
   (d) pulverizing the demineralized bone obtained from step (c).

2. The process for preparing a fibrous demineralized bone matrix of claim 1, wherein the acidic solutions in steps (a) and (c) are, independently of each other, a 0.1 to 3 N HCl solution.

3. The process for preparing a fibrous demineralized bone matrix of claim 2, wherein the acidic solutions in steps (a) and (c) are a 0.6 N HCl solution.

4. The process for preparing a fibrous demineralized bone matrix of claim 1, wherein the pulverizing is carried out to obtain a demineralized bone matrix having a length of from 1000 to 5000 μm.

\* \* \* \* \*